United States Patent
Leong et al.

(10) Patent No.: US 6,837,988 B2
(45) Date of Patent: Jan. 4, 2005

(54) BIOLOGICAL FLUID SAMPLING AND ANALYTE MEASUREMENT DEVICES AND METHODS

(75) Inventors: Koon-wah Leong, Sunnyvale, CA (US); Robert Shartle, Livermore, CA (US)

(73) Assignee: LifeScan, Inc., Milpitas, CA (US)

( * ) Notice: Subject to any disclaimer, the term of this patent is extended or adjusted under 35 U.S.C. 154(b) by 406 days.

(21) Appl. No.: 09/879,146

(22) Filed: Jun. 12, 2001

(65) Prior Publication Data

US 2002/0185384 A1 Dec. 12, 2002

(51) Int. Cl.⁷ .......................... G01N 27/327; A61B 5/05
(52) U.S. Cl. ............... 205/792; 205/777.5; 204/403.01; 204/403.11; 600/345; 600/347
(58) Field of Search ................. 204/403.01, 403.02, 204/403.04, 403.05, 903.11; 205/777.5, 792; 600/345, 347, 365

(56) References Cited

U.S. PATENT DOCUMENTS

| | | | |
|---|---|---|---|
| 5,161,532 A | 11/1992 | Joseph | |
| 5,231,028 A | * 7/1993 | Mullen | 205/188 |
| 5,304,468 A | 4/1994 | Phillips et al. | |
| 5,529,752 A | 6/1996 | Pontis et al. | |
| 5,563,042 A | 10/1996 | Phillips et al. | |
| 5,582,184 A | 12/1996 | Erickson et al. | |
| 5,746,217 A | 5/1998 | Erickson et al. | |
| 5,820,570 A | 10/1998 | Erickson et al. | |
| 5,821,399 A | * 10/1998 | Zelin | 73/1.02 |
| 5,879,310 A | 3/1999 | Sopp et al. | |
| 5,879,367 A | 3/1999 | Latterell et al. | |
| 5,942,102 A | 8/1999 | Hodges et al. | |
| 6,059,946 A | * 5/2000 | Yukawa et al. | 204/403.14 |
| 6,080,116 A | 6/2000 | Erickson et al. | |
| 6,083,196 A | 7/2000 | Trautman et al. | |
| 6,091,975 A | 7/2000 | Daddona et al. | |
| 6,162,611 A | 12/2000 | Heller et al. | |
| 6,379,324 B1 | 4/2002 | Gartstein et al. | |

FOREIGN PATENT DOCUMENTS

| | | |
|---|---|---|
| WO | WO 97/00441 | 1/1977 |
| WO | WO 97/42888 | 11/1997 |
| WO | WO 98/00193 | 1/1998 |
| WO | WO 98/34541 | 8/1998 |
| WO | WO 99/13336 | 3/1999 |
| WO | WO 89/27852 | 6/1999 |
| WO | WO 99/64580 | 12/1999 |
| WO | WO 00/35530 | 6/2000 |
| WO | WO 00/45708 | 8/2000 |
| WO | WO 00/57177 | 9/2000 |
| WO | WO 00/74763 | 12/2000 |
| WO | WO 00/74765 | 12/2000 |

* cited by examiner

Primary Examiner—Kaj K. Olsen
(74) Attorney, Agent, or Firm—Carol M. LaSalle; Bozicevic, Field & Francis, LLP

(57) ABSTRACT

A device for sampling a biological fluid and measuring a target analyte within the biological fluid is provided. The device has at least one micro-piercing member used to penetrate the skin to a selected depth and access biological fluid, a sampling means and a measuring means. The sampling means comprises a fluid transfer medium, such as a hydrophilic porous material, by which sampled biological fluid is transferred from the micro-piercing member to the measuring means. The measuring means includes an electrochemical cell having at least one porous electrode and, typically, a reagent material, where the electrochemical cell is configured so as to make an electrochemical measurement of a target analyte in accessed biological fluid present therein. Methods of sampling biological fluids within the skin and measuring the sampled fluids are also provided, as well as kits comprising one or more of the inventive devices.

38 Claims, 2 Drawing Sheets

BIOLOGICAL FLUID SAMPLING AND ANALYTE MEASUREMENT DEVICES AND METHODS

FIELD OF THE INVENTION

This invention is related to percutaneous biological fluid sampling and analyte measurement, and more particularly to fluid transfer mediums to facilitate sampling of biological fluid.

BACKGROUND

The detection of analytes in biological fluids is of ever increasing importance. Analyte detection assays find use in a variety of applications, including clinical laboratory testing, home testing, etc., where the results of such testing play a prominent role in the diagnosis and management of a variety of disease conditions. Common analytes of interest include glucose, e.g., for diabetes management, cholesterol, and the like.

A common technique for collecting a sample of blood for analyte determination is to pierce the skin at least into the subcutaneous layer to access the underlining blood vessels in order to produce localized bleeding on the body surface. The accessed blood is then collected into a small tube for delivery and analyzed by testing equipment, often in the form of a hand-held instrument having a reagent test strip onto which the blood sample is placed. The fingertip is the most frequently used site for this method of blood collection due to the large number of small blood vessels located therein. This method has the significant disadvantage of being very painful because subcutaneous tissue of the fingertip has a large concentration of nerve endings. It is not uncommon for patients who require frequent monitoring of an analyte, to avoid having their blood sampled. With diabetics, for example, the failure to frequently measure their glucose level on a prescribed basis results in a lack of information necessary to properly control the level of glucose. Uncontrolled glucose levels can be very dangerous and even life-threatening. This technique of blood sampling also runs the risk of infection and the transmission of disease to the patient, particularly when done on a high-frequency basis. The problems with this technique are exacerbated by the fact that there is a limited amount of skin surface that can be used for the frequent sampling of blood.

To overcome the disadvantages of the above technique and others that are associated with a high degree of pain, certain analyte detection protocols and devices have been developed that use micro-piercing, micro-cutting elements or analogous structures to access the interstitial fluid within the skin. The micro-needles are penetrated into the skin to a depth less than the subcutaneous layer so as to minimize the pain felt by the patient. The interstitial fluid is then sampled and tested to determine the concentration of the target analyte. Some kind of mechanical or vacuum means is often used in conjunction with the micro-piercing elements in order to remove a sample of interstitial fluid from the body. Typically, this is accomplished by applying a pressure differential of approximately 6 mm Hg.

For example, International Patent Application WO 99/27852 discloses the use of vacuum pressure and/or heat to increase the availability of interstitial fluid at the area of skin in which the vacuum or heat is applied. The vacuum pressure causes the portion of skin in the vicinity of the vacuum to become stretched and engorged with interstitial fluid, facilitating the extraction of fluid upon entry into the skin. Another method is disclosed wherein a localized heating element is positioned above the skin, causing interstitial fluid to flow more rapidly at that location, thereby allowing more interstitial fluid to be collected per given unit of time.

Still other detection devices have been developed which avoid penetration of the skin altogether. Instead, the outermost layer of skin, called the stratum corneum, is "disrupted" by a more passive means to provide access to or extraction of biological fluid within the skin. Such means includes the use of oscillation energy, the application of chemical reagents to the skin surface, etc. For example, International Patent Application WO 98/34541 discloses the use of an oscillation concentrator, such as a needle or wire, which is positioned at a distance from the skin surface and caused to vibrate by means of an electromechanical transducer. The needle is immersed in a receptacle containing a liquid medium placed in contact with the skin. The mechanical vibration of the needle is transferred to the liquid, creating hydrodynamic stress on the skin surface sufficient to disrupt the cellular structure of the stratum corneum. International Patent Applications WO 97/42888 and WO 98/00193 also disclose methods of interstitial fluid detection using ultrasonic vibration.

Despite the work that has already been done in the area of minimally invasive analyte testing, there is a continued interest in the identification of new analyte detection methods that are less expensive and eliminate the need for ancillary equipment (e.g., oscillation, suction and heat generating devices). Of particular interest would be the development of a minimally invasive analyte detection system that is inexpensive, easy to use, is integratable into a single component and is safe and efficacious.

RELEVANT LITERATURE

U.S. Patents of interest include: U.S. Pat. Nos. 5,161,532, 5,582,184, 5,746,217, 5,820,570, 5,879,310, 5,879,367, 5,942,102, 6,080,116, 6,083,196, 6,091,975 and 6,162,611. Other patent documents and publications of interest include: WO 97/00441, WO 97/42888, WO 98/00193 WO 98/34541, WO 99/13336, WO 99/27852, WO 99/64580, WO 00/35530, WO 00/45708, WO 00/57177, WO 00/74763 and WO 00/74765A1.

SUMMARY OF THE INVENTION

Percutaneous sensor systems and devices, as well as methods for using the same are provided by the subject invention. A feature of the subject devices is the presence of a fluid transfer medium that transfers biological fluid accessed within the skin to a measurement means for measurement of a targeted analyte within the fluid sample. The present invention finds use in the sampling of biological fluids such as blood and interstitial fluid, and in the detection and measurement of various analytes, e.g., glucose, cholesterol, electrolytes, pharmaceuticals, or illicit drugs, and the like, present in the sampled biological fluid. The present invention is especially well-suited for the sampling of interstitial fluid and the measurement of the concentration of glucose therein.

In general, the subject devices include (1) at least one sampling means in the form of a fluid transfer medium and having a distal surface configured to pierce the skin surface and to provide access to biological fluid within the skin, and (2) a measuring means in the form of an electrochemical cell, a porous matrix having a signal producing system, or the like in fluid communication with the sampling means.

The fluid transfer medium is porous, having either a uniform porosity or a gradient of porosity from one portion or end to another portion or end. Preferably, the fluid transfer medium is more porous at a proximal end than towards a distal end, e.g., there is a porosity gradient from the proximal to distal end. The change in porosity from one end to the other end may be gradual or sharp wherein the distal surface is the densest portion (i.e., has the fewest number of pores or none at all) of the fluid transfer medium to provide rigidity when piercing the skin. The fluid transfer medium is made, at least in part, of one or more hydrophilic materials formed in a porous structure having a plurality of pores. As such, the pores provide a capillary action by which the fluid transfer medium is able to transfer fluid.

In certain embodiments, the skin-piercing function is accomplished by the distal surface of the fluid transfer medium. Specifically, the distal surface is formed with very sharp protrusions. In some of these embodiments, this distal surface is non-porous wherein the protrusions have a porous central core that extends through the distal surface, thereby defining a fluid access opening to access biological fluid. The fluid transfer medium extends between the access opening of the micro-piercing member to the measurement means of the subject invention, and functions to transfer biological fluid and/or its constituents present at the access opening to the measurement means. Still, in other embodiments, the entirety of the protrusions are also porous but to a much lesser extent than the proximal region. In these embodiments, an access opening is unnecessary since the porous protrusions themselves allow access of fluid into the sensor device.

Other embodiments of the subject devices have skin-penetrating means discrete from the fluid transfer medium, such as an array of micro-needles comprised of a nonporous material, wherein each of the micro-needles has a distal access opening. The micro-needle side of the array (i.e., the underside of the device) may itself be formed of or coated with an insulating material. In still other embodiments, the micro-needles are made of or coated with a conductive material, such as a metal, to form a set of electro-sensors.

The subject devices which employ an electrochemical cell as the measurement means preferably provide a redox reagent system or material within the electrochemical cell between the electrodes, often called the reaction cell or chamber. The target analyte of the biological fluid present within the reaction chamber, chemically reacts with the redox reagent system to produce an electrical signal measured by the electrodes from which the concentration of the target analyte can be derived. The particular redox reagent material used is selected based on the analyte targeted for measurement. As would be apparent to one of skill in the art, the subject invention may also be modified for use with calorimetric or reflectance-type analyte measuring systems, where such reflectance systems typically comprise a porous matrix containing a signal producing system and a reflectance measuring apparatus which is activated upon a change in reflectance of the matrix when fluid penetrates the matrix. Examples of such systems may be found in U.S. Pat. Nos. 5,563042, 5,563,031, 5,789,255 and 5,922,530, which are herein incorporated by reference in their entirety.

The subject sensor devices may function as a part of an analyte sensing system that includes a means for controlling the sensor device. Specifically, a control unit is provided in which the control means is electrically coupled with the sensor device and functions to generate and send input signals to the electrochemical cell and to receive output signals from the cell. These functions, among others, are performed by a software algorithm programmed within the control unit that automatically calculates and determines the concentration of the target analyte in the biological sample upon receipt of an output signal from the electrochemical cell or a matrix comprising a signal producing system.

Also provided by the subject inventions are methods for using the subject devices and systems as well as kits for use in practicing the methods of the subject invention.

The subject invention is useful for analyte concentration measurement of a variety of analytes and is particularly suited for use in the measurement of glucose concentration in interstitial fluid.

DETAILED DESCRIPTION OF PREFERRED EMBODIMENTS

Percutaneous biological fluid, e.g., interstitial fluid, sampling and analyte measurement sensor devices and systems, as well as methods for using the same, are provided.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a chamber" includes a plurality of such chambers and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In general, the devices of the subject invention include a biological fluid sampling means configured to pierce a skin surface and an analyte measurement means. More specifically, the subject devices, i.e., sensor devices, include at least one sampling means in the form of a fluid transfer medium and having a distal surface configured to pierce the skin surface and to provide access to biological fluid within the skin, and a measuring means in fluid communication with the sampling means. The measuring means of the present invention may comprise any suitable means, including an electrochemical, calorimetric or photometric means or the like. For purposes of this description, an electrochemical cell configuration is described as an exemplary embodiment of the measuring means of the present invention.

The fluid transfer medium is hydrophilic and is primarily comprised of a porous material having a plurality of pores or voids throughout the medium (except in those embodiments in which the fluid medium has a non-porous distal surface) which are sufficiently large and interconnected to permit passage of fluid materials there through. The pores exert a capillary force on the biological fluid, causing the sample fluid and its constituents, to be drawn or wicked into the pores.

The more porous the transfer medium, the faster the fluid travels through the transfer medium, thereby reducing the sampling and measuring time. Additionally, a high pore density increases the volume of fluid capable of passing through the fluid transfer medium per unit of time. However, the more porous a material, the weaker it may be. Thus, in a preferred embodiment, the distal portion of the fluid transfer medium (i.e., the portion configured to pierce the skin) is less porous (i.e., contains fewer pores) than the proximal portion (i.e., the portion associated with the electrochemical cell, discussed below). As such, the distal portion of the fluid transfer medium provides rigidity and strength to ensure that the portion configured to pierce the skin, e.g., the skin piercing structure(s), does not break or crack upon insertion into the skin. Conversely, the porous proximal portion facilitates and expedites the transfer of sampled biological fluid into the electrochemical cell.

In certain embodiments, at least a portion of the less porous distal portion is nonporous. For example, the non-porous portion of the distal portion may be an exterior layer wherein this non-porous exterior layer forms an outer coating or shell that is strong enough to pierce the skin, i.e., the exterior layer functions as the skin piercing structure. However, a center core of the non-porous exterior remains porous and defines an access opening therein in order to allow biological fluid to be wicked into the sensor device. As just described, the exterior layer is made of the same material as the remainder of the fluid transfer medium. In other embodiments, however, this outer layer comprises a different material which acts more as a housing structure for the fluid transfer medium, as well as providing the piercing structures of the invention. Yet in other embodiments, the exterior layer of the less porous distal portion of the fluid transfer medium is not completely pore-less, having enough rigidity to pierce the skin without breaking or cracking yet able to assist in the wicking process.

The more porous, proximal portion of the fluid transfer medium increases the amount and rate at which the sampled biological fluid enters the electrochemical cell. The proximal portion of the fluid transfer medium generally has from about 10 to 100 times, but may have more or less, as many pores as the distal portion. The pore density within the transfer medium preferably increases gradually and consistently from the end of the distal portion to the end of the proximal portion.

As described above, the fluid transfer medium is made of a porous hydrophilic material. Preferably, the material is not water-absorbent such that the water within the biological fluid is not absorbed by the fluid transfer material but is completely passed through the medium along with the other components of the biological fluid. Porous hydrophilic materials usable as the fluid transfer medium include, but are not limited to, polymers, ceramics, glass and silica. Suitable polymers include polyacrylates, epoxies, polyesters, polycarbonate, polyamide-imide, polyaryletherketone, polyetheretherketone, polyphenylene oxide, polyphenylene sulfide, liquid crystalline polyesters, or their composites. Examples of ceramics are aluminum oxide, silicon carbide and zirconium oxide.

A hydrophilic gel or the like may also be used in conjunction with the porous material to form the fluid transfer medium. Suitable gels include natural gels such as agarose, gelatin, mucopolysaccharide, starch and the like, and synthetic gels such as anyone of the neutral water-soluble polymers or polyelectrolytes, such as polyvinyl pyrrolidone, polyethylene glycol, polyacrylic acid, polyvinyl alcohol, polyacrylamide, and copolymers thereof.

Other embodiments of the subject devices have skin-penetrating means on the underside of the device discrete from the fluid transfer medium, such as an array of micro-piercing structures or micro-needles comprised of a non-porous material. For example a non-porous material may be coated over the fluid transfer medium to form micro-piercing structures, e.g., micro-needles or the like. Each of the micro-piercing structures has a distal access opening to provide access to biological fluid. As such, certain embodiments of the subject invention have a layered configuration in which the proximal side of an array of micro-needles is covered by a layer of porous material, e.g., fluid transfer medium, which is then covered by a first conductive layer which is also porous. This layered structure provides a fluid transfer pathway through which biological fluid can travel. A second conductive layer is spaced-apart from the first conductive layer, forming a space, i.e., an electrochemical cell, into which biological fluid is transferred to be tested and measured for analyte concentration. The resulting layered structure may also have a layer, made of insulating material, for example, over the second conductive layer for isolating the electrochemical cell and for housing the device.

The micro-needle or under side of the device may itself be formed of or coated with an insulating material. In still other embodiments, the micro-needles may be additionally or alternatively coated with a conductive material, such as a metal, to form a set of electro-sensors. The electro-sensors may be employed to monitor certain physiological signals or events or may themselves be used as reference electrodes of an electrochemical cell, as is further described below.

In all embodiments of the subject invention, the micro-protrusions or microneedles are configured to be mechanically stable and strong enough to penetrate the stratum corneum without breaking. Preferably, they are made of a biocompatible material so as not to cause irritation to the skin or an undesirable tissue response. Although the sensor devices may be disposable, for those that are intended to be reusable, it is preferable that the material of the micro-needles is able to withstand sterilization cycles.

The electrochemical measurement cell of the subject invention comprises an electrode configuration and a reaction chamber or zone. The electrode configuration includes two spaced-apart electrodes positioned such that a surface of one electrode faces a surface of the other electrode. Preferably, the electrodes are substantially planar and parallel to each other. This spaced apart area defines the reaction chamber in which the sampled biological fluid is tested for the concentration of a target analyte. A redox reagent system or material, selected according to the type of analyte being targeted for measurement, may be used within the electrochemical cell to facilitate the measurement process.

At least one of the electrodes of the subject electrochemical cell is porous. More specifically, a first or distal electrode is porous. Accordingly, the proximal porous portion of the fluid transfer medium is positioned such that its proximal surface is flush against the outer surface of this first porous electrode. This electrode is made of a metalisized porous material, such as the type of porous material used for the fluid transfer medium. Similar to the function of the fluid transfer medium, the porous electrode exerts a capillary force on the sampled biological fluid within the fluid transfer medium causing the fluid to be drawn or wicked through the porous electrode into the reaction chamber, e.g., at least the target analyte of interest is wicked through the porous electrode into the reaction chamber.

The second or proximal electrode may be entirely comprised of a solid conductive material or may have a rigid porous structure, such as a metalized porous material, in which the pores run through the majority of the structure and are much smaller than those of the first electrode. In the latter configuration, i.e., wherein the second electrode has a porous structure, the pore sizes of the second electrode are sufficiently small to create a capillary force on fluid in contact with it thereby causing the fluid within the reaction zone to be drawn or wicked through the second electrode. This configuration facilitates the continuous wicking of the sampled biological fluid within the electrochemical cell thereby purging or displacing air within the cell. The presence of air in the cell can interfere with the analyte measurement. Alternatively, a conventional coplanar electrode pair can be used instead of the top electrode. The subject device may further provide a layer of insulating material over the second electrode for isolating the electrochemical cell and for housing the device. With embodiments having a porous proximal electrode, as just described, one or more vent holes may be formed or made within the housing adjacent the electrode.

Various types of electrochemical systems and methods commonly known in the art of analyte detection and measurement may be employed by the present invention, including systems that are amperometric (i.e., measure current), coulometric (i.e., measure electrical charge) or potentiometric (i.e., measure voltage). Examples of these types of electrochemical measurement systems are further described in U.S. Pat. Nos.: 4,224,125; 4,545,382; and 5,266,179; as well as WO 97/18465 and WO 99/49307; the disclosures of which are herein incorporated by reference.

In operation, one of the electrodes of the electrochemical cell is used as the reference electrode by which an input reference signal is provided to the sensor from a signal generating means. The other electrode operates as a working electrode which provides an output signal from the sensor to a signal receiving means. Preferably, the reference electrode is located at the bottom, i.e., the first electrode as mentioned above, and the working electrode at the top of the device, i.e., the second electrode as mentioned above. This output signal represents the concentration of the target analyte in the sampled fluid.

The reference and working electrodes are in electrical communication with a control means that sets the input reference signal transmitted to the electrochemical cell, receives the output signal from the electrochemical cell and then derives the concentration level of the analyte within the sample from the output signal, e.g., a means for applying an electrical current between the two electrodes, measuring a change in the current over time and relating the observed change in current to the concentration of analyte present in the electrochemical cell. The concentration of the analyte in the patient's blood is then derived from the concentration level in the fluid sample, the numerical value of which is preferably provided as an output signal to a display means.

Figure 2:
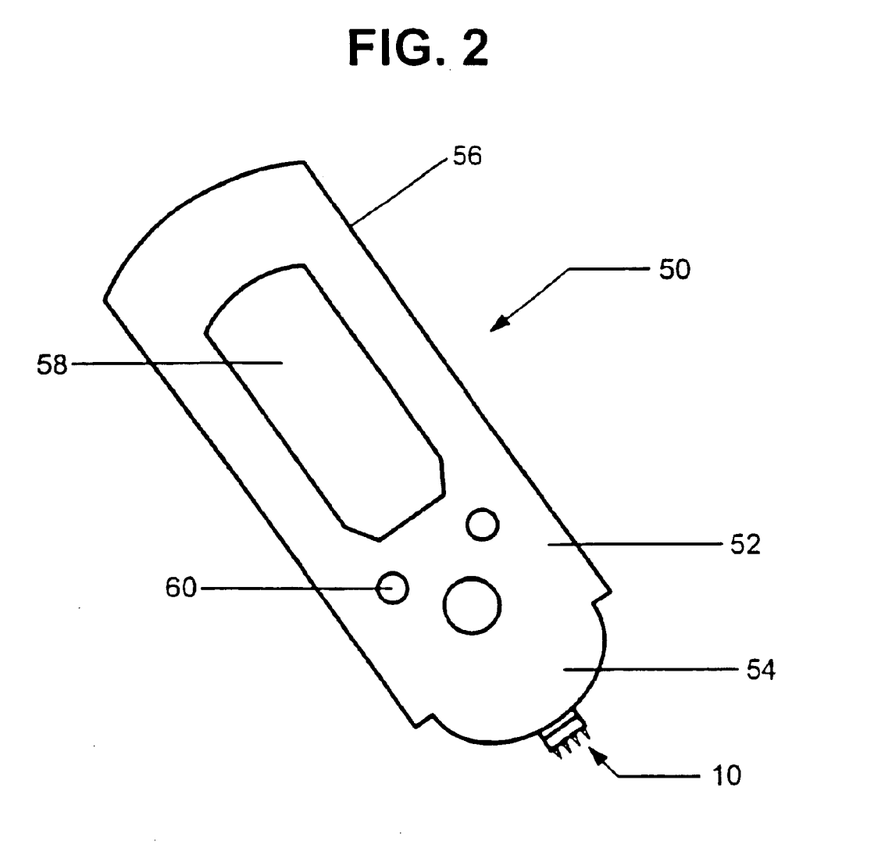
FIG. 2 is a schematic representation of an exemplary hand-held device for using the biological fluid sensing and analyte measuring devices of the present invention.

Preferably, the control and display means are integrally housed within a handheld control unit such as that illustrated in FIG. 2. The control unit preferably also provides a means of securing or holding one or more micro-needles or an array of micro-needles in a position and arrangement suitable for the particular sampling and measuring application at hand.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Exemplary Embodiment of the Device

The general configuration of an exemplary sensor device of the present invention will now be described with reference to FIG. 1. There is shown a sensor device 10 having an array 16 of micro-needles 12 separated by skin-contact surfaces 20. Each micro-needle 12 has a sharp distal tip 14 for easily penetrating through the skin. Distal tip 14 forms an opening within micro-needle 12 for accessing and allowing biological fluids to enter into the sensor device 10.

Here, micro-needles 12 have a conically-shaped configuration but may have any suitable configuration preferably non-tubular, such as a 3- or 4-sided pyramid configuration for example. The shafts of micro-needles 12 may have an annularly-shaped cross-section or any suitable non-annular cross-section, such as a polygonal shape.

The outer diameter of a micro-needle 12 is generally between about 100 to 400 $\mu$m at its thickest point, here the base of the needle, and generally less than about 10 $\mu$m at the tip 14. The average outer diameter of micro-needle 12 is generally between about 100 to 300 $\mu$m, typically between about 120 to 200 $\mu$m.

The length of micro-needles 12 will depend on the desired depth of insertion. More particularly, micro-needles 12 have lengths and sizes within certain ranges depending on the type of biological fluid (e.g., interstitial fluid, blood or both) desired for sampling and the thickness of the skin layers of the particular patient being tested.

As such, target skin layers into which the subject piercing members may be inserted include the dermis, epidermis and the stratum corneum (i.e., the outermost layer of the epidermis). In general, micro-needles 12 have a length of at least about 50 μm and more typically at least about 100 μm, where the length may be as great as 500 μm or greater, but typically does not exceed about 2000 μm and usually does not exceed about 3000 μm.

Any suitable number of micro-needles 12 may be employed by the present invention. The optimal number will depend upon various factors including the agent being detected, the body surface location into which the micro-needles are inserted, the size of the device and the margin of accuracy desired. Regardless of the number micro-needles 12, they are sufficiently separated from each other so as to ensure that the stratum corneum can be penetrated without undue pressure on the skin. In general, micro-needles 12 are separated from adjacent micro-needles a distance, i.e., the length of skin-contact surfaces 20 is in the range from about 10 μm to about 2 mm, and typically from about 100 to 1000 μm, and more typically from about 200 to 400 μm.

Array 16, of micro-needles 12 and skin-contact surfaces 20, defines a bottom portion 18a of a housing 18, the top portion of which is defined by cover 18b. Housing portion 18a provides a support structure for fluid transfer medium 22 and, as discussed above with respect to micro-needles 12, may be made of insulating or conductive materials. As shown in this particular embodiment, micro-needles 12 may be made of the same material and formed integrally with array 16 to form bottom housing portion 18a. Micro-needles 12 may also comprise a porous material and be formed integrally with fluid transfer medium 22. Housing portion 18b is preferably made of an insulating material such as a plastic or a polymer material to isolate the electrochemical cell.

Fluid transfer medium 22 comprises distal portions 22a and proximal portion 22b. Distal portions 22a, respectively, reside within and fill the interior of micro-needles 12. Proximal portion 22b extends into the space defined by the side-walls 24 of bottom housing portion 18a, thus distributing sampled fluid being transported by medium 22 over the extent of the adjacent surface area of the electrochemical cell, discussed in more detail below. As such, fluid transfer medium 22, by means of the plurality of pores therein, provides a pathway for biological fluid to travel from open distal tips 14 to the electrochemical cell positioned above fluid transfer medium 22. Additionally, as discussed above, fluid transfer means 22 provides the capillary action necessary to cause the biological fluid to enter into the sensor device 10 via the openings in distal tips 14. In order to accomplish this transfer at an acceptable rate, size of the pores range from about 0.1 to 50 μm, typically from about 0.1 to 10 μm.

As discussed above, sensor device 10 further comprises measurement means in the form of an electrochemical cell. In FIG. 1, the electrochemical cell comprises a first or bottom electrode 26 and a second or top electrode 28 spaced-apart from each other. The area between electrodes 26 and 28 defines a reaction zone 30 of the cell in which the fluid is tested for the concentration of a target analyte(s). The cell may further contain a redox reagent system or material selected based on the particular target analyte(s). At least a portion of the surfaces of the electrodes that face the reaction zone are comprised of a highly conductive material, such as palladium, gold, platinum, silver, iridium, carbon, doped indium tin oxide, stainless steel and the like, or a combination of such materials. The reagent material, comprising an oxidizing enzyme and an optional mediator component, is deposited on one or both of the facing electrode surfaces.

Electrodes 26 and 28 are preferably parallel to each other to ensure an accurate analyte measurement, and preferably have a planar configuration but may have any suitable configuration or shape such as square, rectangular, circle, etc. The dimensions of the two electrodes are preferably the same, wherein the foot print of each electrode 26, 28 is generally in the range from about 0.1 to 2 $cm^2$, typically between about 0.25 to 1 $cm^2$ The electrodes are very thin, having a thickness generally in the range from about 50 to 1,000 Å, typically from about 100 to 500 Å, and more typically from about 150 to 300 Å.

Preferably, the distance between the electrodes 26, 28 is sufficiently narrow to exert its own capillary force on the biological fluid exposed to the reaction zone. This inter-electrode distance is generally in the range from about 1 to 1,000 μm, typically from about 10 to 300 μm, and more typically from about 10 to 150 μm. In order for the sampled biological fluid within the fluid transfer medium to enter into the reaction zone 30, a fluid pathway between the two areas is necessary. As described in more detail below, bottom electrode 26 may be formed by metallisizing the top surface of the fluid transfer medium 22 with the one or more of the metallic materials mentioned above to provide sufficient conductivity to complete the electrochemical while maintaining some porousity at the top surface of the fluid transfer medium 22. Alternatively, a bottom electrode 26 fabricated from a porous conductive material may be otherwise mounted on this top surface. Thus, bottom electrode 26 provides a fluid pathway and the necessary capillary force to transfer the sampled fluid from the fluid transfer medium into reaction zone 30 while having the necessary conductivity properties to complete the electrochemical cell.

As mentioned above, top electrode 28 may be comprised solely of a non-porous, conductive material, e.g., a solid conductive material formed on the underside of top housing 18b, or may be comprised of a porous conductive material, e.g., a porous conductive material formed on the underside of top housing 18b. As discussed above, the latter configuration facilitates the continuous wicking of the sampled biological fluid within the electrochemical cell thereby purging or displacing air within the cell through one or more tiny air holes within housing cover 18b (not shown).

Manufacturing Techniques

Figure 1A:
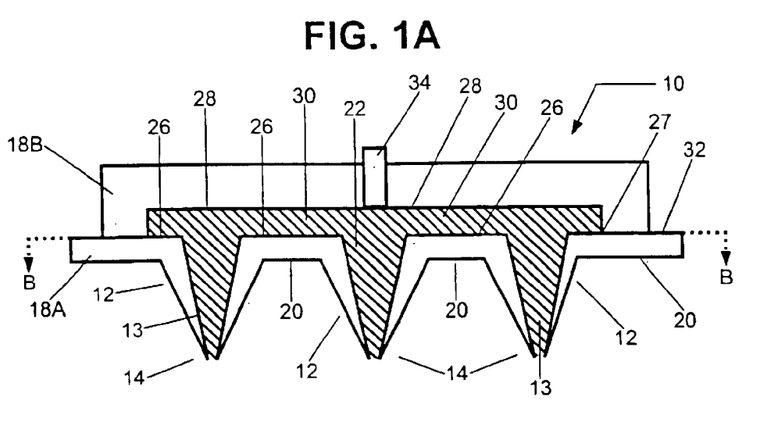
FIG. 1 is a cross-sectional view of an exemplary biological fluid sensing and analyte measuring device of the present invention.
Figure 1B:
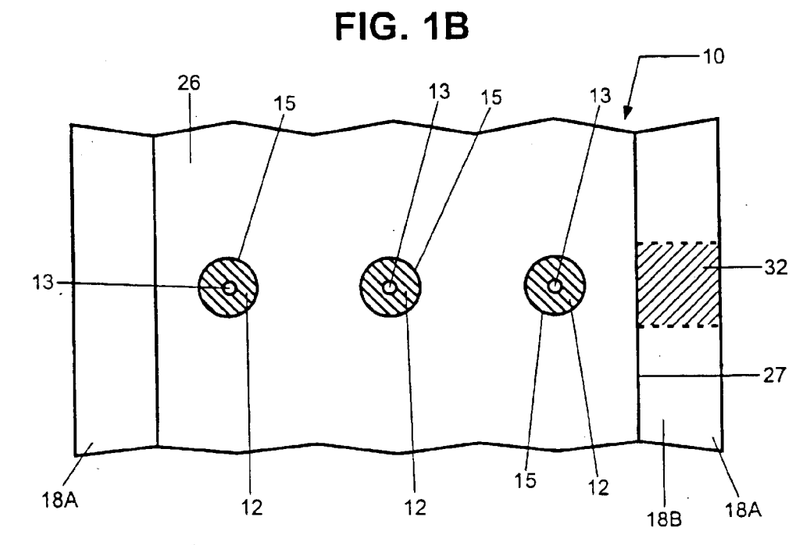

An exemplary method of manufacturing the devices of the present invention, such as sensor device 10 of FIG. 1, comprises the following steps. A hydrophilic material in granulated form is selected for making the porous material of the fluid transfer medium. Suitable hydrophilic materials include, but are not limited to, polymers, ceramics, glass and silica. A powder injection molding process is used wherein fine particles of the selected porous material are mixed with a binder material to form a slurry mixture. The slurry mixture is then forced into a mold having the opposite image of the device and allowed to harden into the desired shape. The molded structure is then placed in a solvent or heated to extract the binding material from the structure. To form the portions of the fluid transfer member on which the micro-needles are formed, a sintering process is used. The porous structure is heated to a temperature high enough to cause the outer surface of the structure to become harder and very strong. Upon cooling, the tips of the micro-needles are then gently ground to create openings to the porous interior. Similarly, the proximal or top surface of the fluid transfer medium is rendered porous by gently grinding the sintered surface in order to expose the porous medium. To form the porous bottom electrode, such as bottom electrode 26 of FIG. 1, a metallic material such as at least one of those metallic materials listed above, is deposited on the proximal or top surface of the fluid transfer medium by sputtering, plasma deposition or electro-deposition techniques, for example. The metallising is performed in a manner and with an amount of metallic material such that the resulting conductive layer is porous. Additionally, an amount of the conductive material is also deposited on at least a portion of the edge of the side wall of the array/bottom housing portion to form a first conductive contact 32 external to housing 18. The top portion 18b of the housing 18 and the top, second electrode 28 of the electrochemical cell may be manufactured with the same or similar materials and techniques described above with respect to the manufacturing of the micro-needle array 16 (which also acts as the bottom housing portion 18a) and bottom electrode 26, respectively. A small hole or bore formed through housing 18b becomes filled with the conductive material when deposited on the underside of housing 18b to form the second electrode 28, forming a second conductive contact 34 external to housing 18. The resulting housing portions 18a, 18b are then sealed together to form sensor device 10. First and second conductive contacts 32 and 34 provide the means for electrically coupling sensor device 10 to control unit such as the hand-held control unit 50 of FIG. 2.

Reagents

To be able to single out and sense the analyte selected to be analyzed over the other analytes in the sampled biological fluid, a specific reagent is used. The reagent may reside on the reactive surface, i.e., the surface facing the porous insulator, of one or both electrodes. Typically this is accomplished by means of an "ink jet" depositing process but other suitable techniques known in the relevant art may also be used.

In many embodiments, the enzyme component of the reagent is an enzyme or a plurality of enzymes that work in concert to oxidize the analyte of interest. In other words, the enzyme component of the reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like. The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the reagent system is a glucose oxidizing enzyme (e.g., a glucose oxidase or glucose dehydrogenase).

The second optional component of the reagent system is a mediator which is made up of one or more mediator agents. A variety of different mediator agents are known in the art and include: ferricyanide, phenazine ethylsulphate, phenazine methylsulfate, phenylenediamine, 1-methoxy-phenazine methylsulfate, 2,6-dimethy-1,4-benzoquinone, 2,5-dichloro-1,4-benzoquinone, ferrocene derivatives, osmium bipyridyl complexes, ruthenium complexes and the like. In those embodiments where glucose in the analyte of interest and glucose oxidase or glucose dehydrogenase are the enzyme components, mediator of particular interest is ferricyanide. Other reagents that may be present in the reaction area include buffering agents, (e.g., citraconate, citrate, phosphate), "Good" buffers and the like.

The reagent is generally present in dry form. The amounts of the various components may vary wherein the amount of enzyme component typically ranges from about 0.1 to 10% by weight.

Exemplary Embodiment of the Sensor System

Referring now to FIG. 2, there is shown a representation of a sensor system 50 of the subject invention. Sensor system 50 comprises a hand-held control unit 52 and a sensor device such as device 10 of FIG. 1 operatively mounted to distal end 54 of control unit 52. Control unit 52 has a housing 56, preferably made of a medical grade plastic material, having a low-profile configuration which houses a means (not shown) for controlling the measurement means of sensor device 10, i.e., generating and transmitting input reference signals to the electrochemical cell of device 10 and receiving output measurement signals from the cell. A software algorithm programmed within control unit 52 automatically calculates and determines the concentration of the target analyte in the biological sample upon receipt of the output signal. The concentration level (among other desired information) is then transmitted to an external display means or screen 58 that displays information to the user. Control interface buttons 60 are provided to allow the user to input information to the control means, such as the type of analyte targeted for measurement.

Sensor device 10 is electrically and physically coupled to control unit 52. Electrical communication between the two is established by means of conductive contacts 32 and 34 on device 10, described with respect to FIG. 1, and corresponding electrical traces (not shown) within control unit 52. Sensor device 10 may be provided in the form of disposable or reusable cartridge. Preferably, sensor device 10 and control unit 52 are physically coupled by a quick lock-and-release mechanism, many of which are commonly known and understood by those of skill in the art, such that a used sensor device can be easily removed and replaced. Control unit 52 is preferably reusable and usable with the plurality of sensor devices of the subject invention, i.e., the control unit 52 is compatible with all of the embodiments of the sensor device described herein. These features facilitate the taking of multiple samples and measurements in an efficient and rapid manner.

Methods

Also provided by the subject invention are methods for using the subject devices and sensor systems to determine the concentration of an analyte in a physiological sample. A variety of different analytes may be detected using the subject sensor systems, where representative analytes include glucose, cholesterol, lactate, alcohol, and the like.

In practicing the subject methods (with reference to the Figures), the first step is to provide a sensor 10, preferably particularly configured (i.e., containing the appropriate reagent) for targeting the analyte(s) of interest. The sensor 10 is operatively engaged and interfaced with a control unit 52 that can be manually held and controlled by the user. Control unit 52 is programmed for testing the targeted analyte(s). The user positions sensor 10 over a selected area of the patient's skin, and, with slight pressure, the micro-needle(s) 12 of sensor device 10 are caused to penetrate into the skin. The depth to which the micro-needles 12 are inserted will depend on the length of the respective micro-needles or by some other means associated with the sensor unit 10 for limiting the insertion depth. Upon insertion into the patient's skin, an amount (i.e., a sample) of biological fluid present at the open tips 14 of micro-needles 12 is wicked through into the less porous distal portion 22a of fluid transfer medium 22. The sampled fluid continues to wick through the porous material into the more porous proximal portion 22b of fluid transfer medium 22. Porous bottom electrode 26 then wicks the sampled fluid into reaction zone 30 where it chemically reacts with the selected reagent.

Following introduction of the fluid sample into the reaction zone, an electrochemical measurement is made by the electrochemical cell. More specifically, an electrical signal (e.g., current, charge, or voltage) generated by the control unit 52 is conducted to bottom electrode 26, called the reference electrode. This "reference signal" passes through the reaction zone. The output signal level, as a result of the electrochemical reaction, is then conducted to the control unit by top electrode 28, called the working electrode. A software algorithm programmed within control unit 52 then automatically determines the differential between the output and reference signals, derives the concentration of analyte in the sample from this differential value, and then derives the corresponding concentration level of the selected analyte in the patient's blood. Any or all of these values may be displayed by display means or screen 58.

A device such as control unit 52 which automatically calculates and determines the concentration of a selected analyte in a biological sample and/or in the patient's system, such that a user need only insert a micro-needle of the subject invention into the patient's skin and then read the final analyte concentration result from a display of the device, is further described in U.S. Pat. No. 6,193,873 entitled "Sample Detection to Initiate Timing of an Electrochemical Assay," the disclosure of which is herein incorporated by reference.

Kits

Also provided by the subject invention are kits for use in practicing the subject methods. The kits of the subject invention include at least one subject sensor device having one or more micro-needles. The kits may also include a reusable or disposable control unit that may be used with reusable or disposable sensor devices of the kit or from other kits of the subject invention. These kits may include sensors having an array of micro-needles having the same or different lengths. Certain kits may include various sensors each containing the same or different reagents. Also, more than one reagent may be provides within a single micro-needle array, wherein one or more of the micro-needles are provided with a first reagent for testing a first target analyte and one or more other micro-needles are provided with other reagents for testing other targeted analytes. Finally, the kits preferably include instructions for using the subject sensors in the determination of an analyte concentration in a physiological sample. These instructions may be present on one or more of the packaging, a label insert, or containers present in the kits, and the like.

It is evident from the above description that the subject inventions are easy to use, eliminating ancillary components for enhancing the amount or velocity of fluid flow within the skin in order to compensate for the negative pressures within the skin. Additionally, the subject inventions provide for the rapid exchange and replacement of sensors, reducing the time necessary for each sampling and measurement activity which is particularly advantageous when administering multiple tests on a single patient or having to test many patients consecutively. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

Although the present invention is useful for many applications, the sampling of various biological fluids and the detection of many types of analytes, the invention has been described primarily in the context of the detection of analytes in interstitial fluids, and as being particularly useful for the detection of glucose in interstitial fluid. Thus, the specific devices and methods disclosed and the applications, biological fluids and analytes discussed herein are considered to be illustrative and not restrictive. Modifications which come within the meaning and range of equivalents of the disclosed concepts, such as those which would readily occur to one skilled in the art, are intended to be included within the scope of the appended claims.

What is claimed is:

1. A biological fluid sampling and analyte concentration measurement device, said device comprising:
   (a) at least one skin-piercing member comprising a biological fluid access opening;
   (b) an electrochemical cell for measuring the concentration of analyte within the biological fluid, wherein the cell comprises at least one porous electrode; and
   (c) a hydrophilic porous material in fluid communication with the at least one piercing member and with the at least one porous electrode, wherein hydrophilic porous material transfers biological fluid present at the access opening of the at least one piercing member to the electrochemical cell, wherein the porous material comprises a distal portion associated with the at least one piercing member and a proximal portion adjacent to the at least one porous electrode, wherein the proximal portion is more porous than the distal portion.

2. The device of claim 1 wherein the proximal portion is about 10 to 100 times more porous than the distal portion.

3. The device of claim 1 wherein the hydrophilic porous material transfers biological fluid by means of a capillary force exerted on the biological fluid in its presence.

4. The device of claim 1 wherein the porous material is selected from the group consisting of polymers, ceramics, glass and silica.

5. The device of claim 1 wherein the electrochemical cell comprises two spaced-apart electrodes defining a reaction chamber and a selected reagent for chemically reacting with an analyte targeted for measurement.

6. The device of claim 5 wherein the distance between the electrodes is from about 10 to 300 microns.

7. The device of claim 6 herein the distance between the electrodes is from about 10 to 150 microns.

8. The device according to claim 5 wherein the reagent is located on a surface of at least one electrode facing the reaction chamber.

9. The device of claim 5 wherein both electrodes are porous.

10. The device of claim 9 further comprising a housing having at least one vent hole for venting air from within the electrochemical cell.

11. The device of claim 1 wherein the biological fluid is interstitial fluid and the analyte is glucose.

12. The device of claim 1 further comprising a hydrophilic gel.

13. The device of claim 1 wherein the hydrophilic porous material comprises pores having diameters in the range from about 0.1 to 50 $\mu$m.

14. The device of claim 13 wherein the pore diameters are in the range from about 0.1 to 10 $\mu$m.

15. A system for sampling biological fluid from the skin of a patient and measuring a target analyte within the biological fluid, the system comprising:
   (a) at least one device according to claim 1; and
   (b) a control means in electrical communication with the at least one device, the control means comprising:

(1) means for sending an electrical input signal to the device and for receiving an electrical output signal from the device, and (2) a software algorithm which automatically calculates and determines the concentration of the target analyte in the biological sample upon receipt of the electrical output signal.

16. The system of claim 15 further comprising a display means in electrical communication with the control means for displaying information in the form of electrical signals received from the control means related to the sampling of the biological fluid and the measuring of the target analyte.

17. The system of claim 16 wherein the device is mounted to the housing by means of a lock-and-release mechanism.

18. The system of claim 15 further comprising a housing wherein the control means is located within the housing and the device is mounted to the housing.

19. The system of claim 18 further comprising user input buttons on the housing for providing user input to the control unit.

20. The system of claim 18 further comprising a display means on the housing for displaying information from the control means.

21. The system of claim 18 wherein the housing has a hand-held configuration.

22. A method for sampling a biological fluid within the skin of a patient and for measuring the concentration of one or more target analytes contained therein, the method comprising the steps of:

providing a biological fluid sampling and analyte measuring system according to claim 15 comprising a first sensor device operatively coupled to a control means;

operatively applying the sensor device to the patient's skin wherein the system samples the patient's biological fluid and measures the concentration of the one or more target analytes therein;

removing the sensor device from the patient's skin;

removing the first sensor device from the control means;

operatively coupling a second sensor device to the control means; and repeating the above steps until the desired number of samplings and measurements have been performed.

23. A kit for sampling a biological fluid from the skin of a patient and for measuring the concentration of a analyte within the sampled biological fluid, the kit comprising:

a system according to claim 15.

24. The kit of claim 23 wherein the biological fluid sampling and analyte concentration measurement device is disposable and the control unit is reusable.

25. A kit for sampling a biological fluid from the skin of a patient and for measuring the concentration of a analyte within the sampled biological fluid, the kit comprising:

a plurality of disposable devices according to claim 1.

26. The kit of claim 25 further comprising a support member wherein the plurality of micro-needles are arranged in an array on the support member.

27. A biological fluid sampling and analyte concentration measurement device, said device comprising:

(a) an array of micro-needles, each micro-needle having an access opening;

(b) a layer of porous material over the array;

(c) a first layer of conductive material over the layer of porous material, wherein the first layer of conductive material is porous and further wherein the access openings, the layer of porous material and the first layer of conductive material provide a fluid transfer pathway; and (d) a second layer of conductive material, wherein the first layer of conductive material and the second layer of conductive material are spaced-apart, wherein biological fluid present at the access openings is caused to be transferred to the space between the first and second layers of conductive material.

28. The device of claim 27 further comprising a layer of insulating material over the second layer of conductive material.

29. The device of claim 27 wherein the array of micro-needles comprises an insulating material.

30. The device of claim 27 further comprising a layer of reagent material between the first and second layers of conductive material wherein an analyte targeted for measurement present in the in the space between the first and second layers of conductive material chemically reacts with the reagent.

31. The device of claim 30 wherein the layer of reagent material contacts either the first layer of conductive material, the second layer of conductive material or both.

32. The device of claim 27 wherein the second layer of conductive material is porous.

33. The device of claim 32, further comprising an insulating layer over the second layer of porous conductive material, wherein the insulating layer has a venting hole there through.

34. The device of claim 27 wherein the biological fluid being sampled is interstitial fluid.

35. The device of claim 35 wherein the analyte is glucose and the reagent comprises a glucose oxidizing enzyme and a mediator.

36. The device of claim 35 wherein the enzyme is selected from a group consisting of glucose oxidase and glucose dehydrogenase.

37. The device of claim 36, wherein the mediator is ferricyanide.

38. The device of claim 27 wherein the micro-needles of the array of micro-needles have varying lengths.

* * * * *